United States Patent
Richardson et al.

(10) Patent No.: US 8,968,771 B2
(45) Date of Patent: Mar. 3, 2015

(54) ARTICLES AND METHODS FOR APPLYING ANTIMICROBIAL PROTECTION

(75) Inventors: Nathan Richardson, Noblesville, IN (US); Dave Parker, Noblesville, IN (US); Scott Kennedy, Anderson, IN (US)

(73) Assignee: Coeus Technology, Inc., Anderson, IN (US)

( * ) Notice: Subject to any disclaimer, the term of this patent is extended or adjusted under 35 U.S.C. 154(b) by 162 days.

(21) Appl. No.: 13/182,776

(22) Filed: Jul. 14, 2011

(65) Prior Publication Data

US 2013/0017242 A1   Jan. 17, 2013

(51) Int. Cl.
| | | |
|---|---|---|
| A61F 13/00 | (2006.01) | |
| A61K 9/70 | (2006.01) | |
| A01N 25/08 | (2006.01) | |
| A01N 25/34 | (2006.01) | |
| A01N 33/12 | (2006.01) | |

(52) U.S. Cl.
CPC .............. *A01N 25/34* (2013.01); *A01N 33/12* (2013.01)
USPC .......................................... 424/443; 424/409

(58) Field of Classification Search
CPC ........ A01N 33/12; A01N 55/00; A01N 25/34
See application file for complete search history.

(56) References Cited

U.S. PATENT DOCUMENTS

| | | | | |
|---|---|---|---|---|
| 4,781,974 | A | * | 11/1988 | Bouchette et al. ............. 442/327 |
| 5,846,215 | A | * | 12/1998 | Zygmont ........................... 604/1 |
| 6,613,755 | B2 | * | 9/2003 | Peterson et al. ................. 514/63 |
| 6,673,358 | B1 | * | 1/2004 | Cole et al. ...................... 424/404 |
| 6,994,890 | B2 | * | 2/2006 | Ohlhausen et al. ......... 427/393.4 |
| 7,014,062 | B2 | * | 3/2006 | Parris et al. ...................... 221/34 |
| 8,257,780 | B2 | * | 9/2012 | Ohlhausen et al. ............. 427/62 |
| 2003/0129419 | A1 | * | 7/2003 | Chen ............................. 428/447 |
| 2006/0110348 | A1 | * | 5/2006 | Ohlhausen et al. .......... 424/70.1 |
| 2009/0223411 | A1 | * | 9/2009 | Higgins et al. ............. 106/287.1 |
| 2010/0167613 | A1 | * | 7/2010 | Higgins et al. ................ 442/123 |

OTHER PUBLICATIONS

Fisher Scientific website, Kimberly-Clark Kimwipes Delicate Task Wipers, 2012.*

* cited by examiner

*Primary Examiner* — Brian-Yong Kwon
*Assistant Examiner* — Mark V Stevens
(74) *Attorney, Agent, or Firm* — Woodard, Emhardt, Moriarty, McNett & Henry LLP

(57) ABSTRACT

Among other things, there is disclosed an improved wet wipe or similar substrate for applying an antibacterial/antibiotic layer to surfaces or other items. A wipe substrate is impregnated with a solution in water of organo-functional silane-based molecule, such as 3-(trihydroxysilyl) propyldimethyloctadecyl ammonium chloride and/or octadecyldimethyl trimethoxysilylpropyl ammonium chloride. Packages of multiple wipes for a consumer's pocket, home, business or other uses are also discussed.

16 Claims, No Drawings

ARTICLES AND METHODS FOR APPLYING ANTIMICROBIAL PROTECTION

The present disclosure concerns application of lasting antimicrobial protection to work surfaces, tools and other substrates. In particular, this disclosure features methods and products for easy and straightforward wiping on of a long-lasting layer of antimicrobial protection.

BACKGROUND

It has long been known to clean or sterilize a surface or item by spraying an antiseptic liquid onto a cloth or directly onto a surface or item, and wiping the surface or item with the sprayed cloth is only a temporary solution to the problem of microbe contamination. Such antiseptic liquids commonly include alcohol or alcohol-based compositions, which are well-known to have anti-bacterial properties. Spraying such compositions on a cloth and using the sprayed cloth to wipe a surface, or spraying a surface with such a composition and wiping it, acts in two ways. First, the contact of the spray or the sprayed area of the cloth against the surface to be wiped results in a contact-killing of a percentage of microbes on the surface. Second, the sprayed composition that transfers or lies on the surface maintains the antibiotic effect for as long as the wet composition remains. However, given the high volatility of alcohol, the composition remains on the surface only for a matter of seconds or perhaps minutes. Such compositions are frequently not evenly spread across a surface, with some areas receiving a substantial amount of the composition, and other receiving a small amount or none at all. Once the composition is gone, e.g. by evaporation, its antibiotic effect is naturally also gone.

Such antiseptic compositions have also been applied to wipes or disposable towelettes. Such towelettes have an amount of an alcohol solution or composition applied to them, and they are stored in a package for individual retrieval and use. The towelettes can be used to wipe a surface, tool or other item to kill topical microbes. Such protection lasts only while any composition that may transfer to the wiped surface remains on the surface in a form permitting it to chemically affect microbes.

There have also been compositions developed for application directly in a manufacturing process to provide anti-microbial protection for products. For example, the active ingredient 3-(trihydroxysilyl) propyldimethyloctadecyl ammonium chloride is provided for industrial uses as a thick suspension, and may be used in or during manufacture of clothing, building materials or other products, so that the products have a resistance or shield from bacterial or other microbial attachment to the product. These compositions are specifically formulated for application in manufacturing the particular products to which they are applied. It has been reported that the antimicrobial protection provided by 3-(trihydroxysilyl) propyldimethyloctadecyl ammonium chloride as applied in manufacturing lasts over very long periods and through regular washing of the product. That is, the protection remains fixed to the article to which it is applied.

Currently there are are no products available that are used to transfer the antimicrobial properties of organo-functional silane-based molecules such as 3-(trihydroxysilyl) propyldimethyloctadecyl ammonium chloride from a carrier object to which they are applied to another object or surface. Compositions suitable for such transfers have not been found. There is a need for products suited to easy transfer of such compositions in consumer-oriented or similar contexts.

SUMMARY

Among other things, the inventors have successfully developed a disposable wipe impregnated with a liquid solution of an organo-functional silane-based molecule that transfers a layer of the solution to a surface. Two particular examples of active ingredients that have been determined to be preferable in the current disclosure are 3-(trihydroxysilyl) propyldimethyloctadecyl ammonium chloride and octadecyldimethyl trimethoxysilylpropyl ammonium chloride. It has been found that each of these substances individually provide an antimicrobial layer that is mechanical in operation, as opposed to chemical barriers provided by alcohols, phenols and other antibacterial substances. The latter substances react with microbes to alter their chemistry or that of their surroundings so that they cannot survive. The antimicrobial effect of those substances last only as long as the active chemical(s) are in liquid form, to enter or attack the microbes they touch. Once such antimicrobials or their solvents evaporate, however, their activity against microbes is severely diminished or eliminated. Certain types of quaternary ammonium molecules are known for topical chemical disinfectant properties. Like alcohols and other chemical disinfectants, their efficacy essentially ends when they dry or evaporate.

A solution of 3-(trihydroxysilyl) propyldimethyloctadecyl ammonium chloride and/or octadecyldimethyl trimethoxysilylpropyl ammonium chloride in water has been found to be suitable to use to soak a flexible substrate to created a disposable wipe. The wipe can be used to wipe a variety of surfaces, tools, products or other items, with a portion of the solution transferring to the wiped surface. The solution dries, by evaporation at room temperature, by applying heat or blowing air over the wiped surface, or by other methods, leaving a layer, coating or film of 3-(trihydroxysilyl) propyldimethyloctadecyl ammonium chloride and/or octadecyldimethyl trimethoxysilylpropyl ammonium chloride, which bonds to the surface to provide semi-permanent antimicrobial protection.

Silane-based quaternary ammonium compounds in solution have been found to have a longer-lasting antimicrobial effect than existing preparations using other quaternary ammonium ions or compounds. These longer-lasting compounds provide a layer or coating that physically destroys microbes, and in the process the layer or coating is not used up, as is the case with antimicrobial preparations that kill microbes chemically. This disclosure provides such benefits in a new, consumer-friendly way.

The disclosure includes an article for imparting an antimicrobial layer onto a surface that includes a flexible absorbent substrate and a solution impregnated into the substrate. The solution contains an organo-functional silane-base quaternary ammonium salt at a concentration of between about 0.10 percent to 2.0 percent in water, and the amount of the solution impregnated into the substrate is such that when the substrate is wiped on a surface, a portion of the solution is transferred to the surface. In particular embodiments, the substrate is a wipe, and may also or instead be one of a towelette, a pad, a sachet, and a bandage. Particular organo-functional silane-base quaternary ammonium salts usable in such items are 3-(trihydroxysilyl) propyldimethyloctadecyl ammonium chloride, octadecyldimethyl trimethoxysilylpropyl ammonium chloride, and combinations of them. Effective concentrations of the salt(s) in water may also be between about 0.10 percent and 2.0 percent inclusive.

Such articles are prepared in some embodiments such that when the solution is applied to the surface from the substrate and dries, the antimicrobial layer remains and is effective on the surface. Articles may be provided at least initially within a package for easy storage and access by a consumer or other user. Articles may also be prepared by a user, with the user applying the solution to the substrate prior to using the article to impart an antimicrobial layer to a surface.

Packaged consumer products are contemplated. For example, a product may include a plurality of articles each including a flexible absorbent substrate impregnated with a solution, the solution containing an organo-functional silane-base quaternary ammonium salt (such as 3-(trihydroxysilyl) propyldimethyloctadecyl ammonium chloride, octadecyldimethyl trimethoxysilylpropyl ammonium chloride or combinations thereof) at a concentration of between about 0.10 percent to 2.0 percent in water. A container initially substantially water tight encloses the articles, from which said articles can be withdrawn. When one or more of the articles are withdrawn from the container, each such withdrawn article is capable of transferring at least a portion of the solution from itself to a surface, so that the surface has an antimicrobial layer after the solution dries on the surface. Concentrations as noted above (e.g. between about 0.10 percent and 2.0 percent inclusive) of the salt are effective.

Methods of making and using such articles or related products are also disclosed. For example, a method of cleansing a surface and leaving a dry antimicrobial layer includes wiping a flexible substrate impregnated with a solution on a surface, with the solution containing an organo-functional silane-base quaternary ammonium salt (such as 3-(trihydroxysilyl) propyldimethyloctadecyl ammonium chloride, octadecyldimethyl trimethoxysilylpropyl ammonium chloride or combinations thereof) at a concentration of between about 0.10 percent to 2.0 percent in water. The wiping transfers at least a portion of the solution from the substrate to the surface so that a layer of solution is present on at least a portion of the surface. Drying the layer on the surface is performed, so that a semi-permanent layer of the organo-functional silane-base quaternary ammonium salt is fixed to the surface, with the layer providing continuous anti-microbial protection after the drying occurs. Such drying can be accomplished through evaporation of the water from the solution at room temperature, or by applying heat or increased airflow, as examples. The substrate can be removed from a container having at least one such substrate.

In another example, a method of making a substrate adapted to lay an antimicrobial layer on a surface includes applying a solution containing an organo-functional silane-base quaternary ammonium salt (such as 3-(trihydroxysilyl) propyldimethyloctadecyl ammonium chloride, octadecyldimethyl trimethoxysilylpropyl ammonium chloride or combinations thereof) at a concentration of between about 0.10 percent to 2.0 percent in water to a flexible substrate, so that the substrate is impregnated with the solution and at least part of the solution remains in liquid form contacting or within the substrate. The applying can include the solution in an amount sufficient to transfer at least a portion of the solution from the substrate to a surface when the substrate is brought into contact with the surface. Such substrates may be disposable and by any one or more of wipes, bandages, pads, sachets, and towelettes. These items can be used to provide a long-lasting antimicrobial layer that is effective after drying to surfaces such as household or business surfaces, skin, frequently handled surfaces, tools, medical devices, and many others.

DESCRIPTION OF PARTICULAR EMBODIMENTS

For the purposes of promoting an understanding of the principles of the disclosure, reference will now be made to the particular embodiments and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

The present disclosure generally concerns new and surprising compositions and methods for making and using an anti-microbial wipe to provide long-lasting antimicrobial protection for surfaces in the home, business or other locations. A flexible substrate is saturated with a liquid composition that is transferable from the substrate to a surface or object. Following such wiping, a semi-permanent layer remains on the surface or object to provide long-term anti-microbial properties for the surface or item. The antimicrobial wipes of the present disclosure are highly efficacious for providing improved germ reduction, and residual antimicrobial effectiveness versus transient bacteria, and do not adversely affect surfaces. Embodiments also do not need or include alcohol as a solvent, with its tendency to dry out materials to which it is applied. While other physical or chemical components might be added, such as surfactants (e.g., phenol ethoxylates, phosphate esters, polyethylene glycols, and/or polypropylene glycols) or inert components, the antimicrobial wipes need no additional components for effective use.

The term "antimicrobial wipe" is used herein to mean products in which a substrate (e.g. a flexible sheet of porous or absorbent material) is impregnated or saturated with a liquid antimicrobial composition for the purpose of rubbing the product over a surface to clean the surface and/or control the growth and viability of transient bacteria. The composition may be applied during manufacturing of a wipe or other product, or may be applied by an individual (e.g. consumer) via a spray bottle, or in other ways. A "wipe" as used herein means a sheet product or substrate used by consumers to wipe or clean surfaces or items or for similar uses, and includes products such as towelettes, sachets, pads, paper towels, and similar items. "Flexible" as applied to a wipe or substrate indicates that the item remains integral or intact during use, but has little rigidity so that it can conform to the user's hand, can be folded if the user desires, and is supple and compliant. It is recognized that customers prefer for cleaning a wipe that has little stiffness while retaining integrity. The term "antimicrobial composition" as used herein means a composition which controls the growth and viability of transient bacteria on a surface to which the composition is applied. The term "saturated" as used herein is intended to mean a state in which liquid can be expelled or transferred from the saturated item to another item, but does not necessarily mean that the saturated item holds all of the liquid it possibly can.

Porous or absorbent sheets or substrates for antimicrobial wipes are well-known, as are methods of making such substrates, and therefore they will not be described in great detail. Such substrates may be formed from woven or nonwoven fiber(s), fiber mixture(s) and/or foam(s) of sufficient wet strength and absorbency to hold an effective amount of the antimicrobial composition. Exemplary woven and nonwoven cloths as substrates are generally made by air- or water-laying processes in which fibers or filaments are cut to desired lengths, passed into a water or air stream, and then deposited onto a screen through which the fiber-laden air or water is passed. The deposited fibers or filaments are then adhesively bonded together, and/or otherwise treated as desired. Such fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters). It will be understood that cloth substrates or other products available in a household, business or industrial environment can also be used, particularly in embodiments in which compositions discussed herein are sprayed onto them prior to wiping a surface.

Antimicrobial compositions as disclosed herein include an active ingredient that is an organo-functional silane-based molecule. Organo-functional silanes are molecules carrying two different reactive groups on their silicon atom so that they can react and couple with very different materials (e.g., inorganic surfaces and organic resins via covalent bonds and often via a polymeric "transition" layer between these different materials). In particular, compositions according to this disclosure use as active ingredients one or both of 3-(trihydroxysilyl) propyldimethyloctadecyl ammonium chloride and octadecyldimethyl trimethoxysilylpropyl ammonium chloride. The silane portion of each molecule generally forms a firm bond to a surface on which the anhydrous molecule lies, so that once applied to an article the molecules cannot thereafter effectively be moved to another item or location. Industrially-available preparations (known to the trade as AEM 5772, AEM 5700, Bio-Protect 7200, AM500, Bioshield 150, Duraban, GoldShield 75, HM4100, Maguard qsx-500, Marquat 72, Sis7200, SIS AM500, Sprots-aide 1000, Zoonocide, Ztrex 72 Antimicrobial mup) including one or both of these molecules are thick suspensions of the molecule(s) in medium to heavy concentrations in methanol or ethanol. These industrial preparations are not consumer-friendly, generally having a high toxicity in available forms, and being too thick or heavy to be effectively used with small, flexible wipes.

It has been surprisingly discovered that compositions can be prepared that include organo-functional silane-based active ingredients, and are able both to be impregnated effectively into a thin, flexible substrate such as those described above and to form an effective antimicrobial barrier when applied from a wipe or substrate to a surface. Solutions of industrially-available preparations (e.g. 3-(trihydroxysilyl) propyldimethyloctadecyl ammonium chloride) were placed in solution with water. It was discovered that at higher concentrations (e.g. at or above about 3 to 4 percent weight/volume) the molecules polymerize to an unsatisfactory degree, making a stable solution either impossible or heavier and unsuitable for saturating a wipe-type substrate or spraying onto a surface or substrate. However, lower concentrations of the molecule in aqueous solution were found to avoid polymerization, so that the solution was amenable to impregnation in a wipe or spraying onto a surface, and also to be effective in providing an antimicrobial layer on use of the wipe. These solutions remain stable in impregnated or saturated substrates (e.g. wipes in a liquid-tight containers) or in a bottle or other container for the solution. These solutions do not suffer from polymerization of the solute or from precipitation of the solute. Surprisingly, the solute remains in the solution after application of the solution to a substrate, without binding to the substrate. When the substrate is used to wipe, the solution with the solute remains on the wiped surface in a layer. As the solvent is dried, by evaporation or otherwise, the solute remains in a dry physical layer that remains to physically combat microbes.

Accordingly, antimicrobial compositions including an organo-functional silane-based molecule in solution with distilled water as the solvent, with the concentration of the molecule low enough to avoid significant polymerization of the molecule and high enough so that transfer of the solution to a surface from a wipe will result in a semi-permanent antimicrobial layer are disclosed, as discussed further below. By "semi-permanent" it is meant that the layer remains in dried form, with anti-microbial properties, after drying of the solvent. The layer can be scraped off or at least partially dislodged by physical engagement, but does not evaporate or blow away with air currents. Concentrations of organo-functional silane-based molecule in distilled water should be preferably below about 10 percent (weight/volume), in preferred embodiments below about 3 percent, such as between about 1 and about 2 percent. Particularly preferred embodiments of antimicrobial composition have between about 1.3 percent and about 1.4 percent concentration (weight/volume) of organo-functional silane-based molecule in distilled water.

As previously noted, two particular active ingredients that are preferred for use in the wipes of the present disclosure are 3-(trihydroxysilyl) propyldimethyloctadecyl ammonium chloride and octadecyldimethyl trimethoxysilylpropyl ammonium chloride. Either or both of these active ingredients are dissolved in distilled water to a concentration as indicated above. For example, 3-(trihydroxysilyl) propyldimethyloctadecyl ammonium chloride in suspension is added to distilled water to form a solution. Preferred concentrations of that solution are about or below 3 percent (weight/volume) of molecule in water, such as between about 1 and about 2 percent. Concentrations of 3-(trihydroxysilyl) propyldimethyloctadecyl ammonium chloride in water between about 1.3 percent and about 1.4 percent concentration (weight/volume), inclusive, have been prepared and tested, with good results. As another example, octadecyldimethyl trimethoxysilylpropyl ammonium chloride in suspension is added to distilled water to form a solution. Preferred concentrations of that solution are about or below 3 percent (weight/volume) of molecule in water, such as between about 1 and about 2 percent. Concentrations of octadecyldimethyl trimethoxysilylpropyl ammonium chloride in water between about 1.3 percent and about 1.4 percent concentration (weight/volume), inclusive, have been prepared and tested, with good results. Combinations of 3-(trihydroxysilyl) propyldimethyloctadecyl ammonium chloride and octadecyldimethyl trimethoxysilylpropyl ammonium chloride are also usable in antimicrobial compositions for wipes. Exemplary concentrations for each molecule are between 0.10 to 2.0% weight/volume inclusive.

As one particular example, antimicrobial compositions were made by dissolving a suspension of 3-(trihydroxysilyl) propyldimethyloctadecyl ammonium chloride (available under the trade-name AEM5700 from Dow Corning via Aegis Environments in distilled water. Particular concentrations of aqueous 3-(trihydroxysilyl) propyldimethyloctadecyl ammonium chloride were prepared. Respective wipes (Kimwipes, Kimberly-Clark Worldwide, Inc., Dallas) were saturated with the respective compositions. It was found that not only did the compositions soak into the wipes sufficiently, in testing the wipes transferred composition to surfaces.

In that testing, the following procedure was used: 30 glass slides were rinsed, wiped with a dry wipe, and dried for 30 minutes. After drying, the slides were divided into three sets of ten. One set was wiped with the test composition wipe, another set with a control wipe consisting of a non-silanated quaternary ammonium disinfecting composition wipe (Lysol-brand), and the final group was not treated with any chemical wipe. After a 30 minute drying period, each slide was placed in a 50 mL Falcon Tube and rinsed 3 times with 50 mL of distilled water. Following this, each slide was again wiped with a dry wipe and allowed to dry for 30 minutes. 20 μL aliquots of distilled water were placed on each slide. Photographs of each slide were taken and then analyzed to determine the contact angle of the water droplet upon the slide. The contact angle of slides wiped with the test composition was on average 33.9° greater than slides wiped with the control composition. The contact angle of slides wiped with the test composition was on average 52.5° greater than slides that had not been treated with any wipe. Contact angle measurements are listed in the table below.

TABLE 1

| Sample | Average Contact Angle | 95% Confidence Limit |
|---|---|---|
| Untreated wipes | 29.7° | 8.0° |
| Control composition wipes | 48.3° | 9.9° |
| Test composition wipes | 82.2° | 1.8° |

The results indicate continued ability of the wiped-on layer to provide a hydrophobic barrier, specifically a bonded layer of the 3-(trihydroxysilyl) propyldimethyloctadecyl ammonium chloride, even after the composition had dried, and the slide had been rinsed and dried again.

In other testing, a challenge culture of S. aureus ($10^7$ CFU/mL) was prepared by diluting an overnight culture into a phosphate buffer. Slides were made by placing 0.5 mL of the challenge culture on individual slides and allowing the culture to dry under ambient conditions. After the slides were dry, samples were treated by (1) wiping with Lysol-brand (non-silanated) chemical wipes, or (2) wiping with test wipes of several discrete concentrations of aqueous 3-(trihydroxysilyl) propyldimethyloctadecyl ammonium chloride solution. Control slides were not wiped. Following treatment with a wipe, slides were rinsed with water and allowed to dry, as were the control slides. Treated and control slides were transferred into 30 mL of buffer and gently agitated for 10 minutes. An analysis of subsisting bacteria was made, and the results indicated that the wiped-on layer reduced viable microbial cell populations even after the composition had dried and the slide had been rinsed and dried again. Particularly high effectiveness in reduction of bacterial population by concentrations of solution of 1.6% and 1.4% was noted.

Antimicrobial compositions as discussed above may be applied to one or more wipes in any of several ways, as may be desired. For example, such compositions may be applied to wipes in the wipe-manufacturing or -packaging process. If wipes are manufactured in a web or sheet, for instance, the dried web can be saturated with a composition as it travels to a packaging station or process. The web of wipes remains wet, i.e. saturated with composition, until packaged, and the packaging is sufficiently water- and air-tight so that the wipes remain saturated for a sufficient shelf-life (e.g. several months). Alternatively, wipes can be manufactured and placed in a temporary or permanent package, and an antimicrobial composition as discussed can be added to the package in an amount sufficient to saturate all of the wipes, and perhaps to allow an amount of the composition to pool in the bottom of the package. Other methods of soaking or saturating individual wipes or groups or sets of wipes may be used.

Packages of wipes according to this disclosure may include multiple wipes saturated with an antimicrobial composition as disclosed. Smaller numbers of saturated wipes (e.g. six or ten) may be provided in a pack sized and configured for carrying in a purse or pocket. Larger numbers of saturated wipes (e.g. 50 or 100) may be provided in a hard plastic or other container for storage in the home, business or other setting. As noted, it is preferred for such packages to be at least initially substantially water- and air-tight so that the wipes remain saturated. The nature of the antimicrobial compositions discussed above are that they are easily transferred from the wipe to a surface, when the active ingredient is in particular concentrations in aqueous solution. When the solution dries, the active ingredient is left bonded to the surface and cannot effectively be transferred from the surface to which it is bonded.

In use, wipes according to the present disclosure are used to place a long-lasting dry antimicrobial coating or shield on a surface, e.g. of a fixture (such as a table or counter top), a tool (such as a scalpel or knife), an item touched by many people (such as a telephone or door handle), or other surfaces that can be susceptible to deposit or collection of microbes. A wipe saturated with a composition as noted above (for this example, aqueous 3-(trihydroxysilyl) propyldimethyloctadecyl ammonium chloride solution at a concentration of 1.3%) is used to wipe the surface to be protected. The wipe may be taken from a package of multiple wipes, as indicated above, or by saturating a dry wipe (e.g. paper towel or household cloth) with the solution. The user contacts the wipe to the surface and runs the wipe along the surface so that a portion of the solution in the wipe is left on the surface. The surface is then dried, e.g. by ambient drying (evaporation) or by active drying with forced air and/or a heat source.

When the surface is dry, i.e. when the solvent in the solution is evaporated or otherwise removed, the active ingredient of aqueous 3-(trihydroxysilyl) propyldimethyloctadecyl ammonium chloride solution remains on the surface. The active ingredient bonds to the surface so as to present a physical barrier to microbes that approach the surface. The bond prevents the active ingredient from being moved off of the surface by air currents. The active ingredient layer or coating can be physically scraped off of the surface, but it has been found that it generally does not wash off of surfaces once dried and bonded.

It is also intended that compositions as noted above may be packaged without wipes, e.g. in a spray bottle or other container, for later application to wipes, cloths or other substrates, or directly to a surface on which a dry antimicrobial layer is desired, by the consumer. Such substrates may not only be those for applying to hard or inanimate surfaces as indicated above, but other types of substrates, such as bandages, pads or similar items used in first aid or other medical applications, which can transfer an antimicrobial layer that remains after drying to skin, tools or other surfaces. Any variety of spray bottle might be used to package, store and dispense compositions disclosed herein. The user may spray a composition as noted above onto a substrate to impregnate or saturate the substrate. The substrate is then contacted with or wiped onto a surface or object, as indicated above, to spread the antimicrobial composition and to create the long-lasting antimicrobial layer on evaporation of water from the composition.

The antimicrobial compositions noted in this disclosure do not require potentially hazardous, damaging or expensive solvents for use. Phenol-based active ingredients (such as triclosan) require alcohol as a solvent. The compositions disclosed above are anionic physical destructors of microbes. They are not chemical barriers or destructors of bacteria and other microbes, as alcohols and other sprayable or wipeable compositions available to consumers are. Such chemical barriers are used up as they attack microbes, and lose efficacy when they dry, so that their usefulness is very short-lived. A physical destructor such as the compositions disclosed above, which remains active and physically attached to a surface until it is physically removed, as by scraping off, has a much longer useful life.

The antimicrobial compositions noted above do not require the chemical additives that many chemical antimicrobials require. As noted above, the active ingredients 3-(trihydroxysilyl) propyldimethyloctadecyl ammonium chloride and octadecyldimethyl trimethoxysilylpropyl ammonium chloride are soluble at low yet effective concentrations in water, obviating the need for other solvents, and reducing hazards relating to toxicity. Binding agents are not necessary in the disclosed compositions. Rather, aqueous solutions as defined herein are applied directly to or saturated directly in the wipe or other similar substrate, and is adequately maintained in or with the substrate until transferred to a surface by wiping. The transfer of the solution, after drying, results in a semi-permanent layer or coating that kills microbes that approach the surface.

Existing formulations of 3-(trihydroxysilyl) propyldimethyloctadecyl ammonium chloride and octadecyldimethyl trimethoxysilylpropyl ammonium chloride are not consumer-friendly, as noted above. Further, they are not formulated to be usable in a thin wipe or similar substrate, as their thickness not only defeats the flexibility and physical usefulness of such substrates, but also are not easily wiped onto a surface or object in a thin and/or uniform, easily evaporatable layer or coating. Existing formulations of these molecules are up to 72 percent molecule (weight/volume) in suspension, which is too thick for consumer use as disclosed. Such high-concentration formulations have a great tendency for the molecule to polymerize if not packaged in tightly sealed containers. Once the containers are opened, the formulation naturally has a very short life.

Formulations useful with a wipe that will transfer an amount of organo-functional silane-base quaternary ammonium salt (such as 3-(trihydroxysilyl) propyldimethyloctadecyl ammonium chloride and/or octadecyldimethyl trimethoxysilylpropyl ammonium chloride) to a surface or product for antimicrobial protection have not been developed, it is believed, because of the unfriendly formulations of such materials that have been available. It is not believed that water solutions of these materials have been created that meet criteria noted above. The uses these items have been put to also have not indicated usefulness with wipe products. The compositions indicated herein provide proper water solutions of active agent (3-(trihydroxysilyl) propyldimethyloctadecyl ammonium chloride and/or octadecyldimethyl trimethoxysilylpropyl ammonium chloride) that transfer an effective amount of antimicrobial protection, yet maintain a pleasant and useful wipe product for the consumer. Optimal ranges for 3-(trihydroxysilyl) propyldimethyloctadecyl ammonium chloride and/or octadecyldimethyl trimethoxysilylpropyl ammonium chloride in water that will stop or limit significant polymerization within a container (e.g. a container that holds wipes as disclosed above) are about 2.3 percent to about 0.0025 percent.

In particular embodiments, the antimicrobial composition has from about 0.10% to about 2.0%, preferably from about 1.0% to about 1.75%, and more preferably from about 1.3% to about 1.4%, by weight of the antimicrobial composition, of the solute, which forms the active antimicrobial ingredient. Non-anionic active ingredients or agents are required in order to avoid interaction with the cationic surfactants of the invention.

It will be understood that the above-described systems, structures and methods are exemplary only, with a variety of other functions and structures being useful as suggested above.

While the disclosure has been described in detail and foregoing description, the same is to be considered as illustrative and not restrictive in character, it being understood that only the preferred embodiment has been shown and described and that all changes and modifications that come within the spirit of the disclosure are desired to be protected. It will be evident from the specification that aspects or features discussed in one context or embodiment will be applicable in other contexts or embodiments.

What is claimed is:

1. A product comprising:
   one or more articles each including a flexible absorbent substrate consisting of a material without polyolefins impregnated with a solution consisting of an organo-functional silane-base quaternary ammonium salt and a solvent, the solvent is at least about 90% water and optionally one or more phenol ethoxylates, polyethylene glycols, and/or polypropylene glycols, wherein the concentration of the organo-functional silane-base quaternary ammonium salt is between about 0.10 percent to 2.0 percent, the solution formulated for transfer of the organo-functional quaternary ammonium salt in solution to a surface from said substrate; and
   a container initially substantially water tight in which said articles are enclosed in the solution, and from which said articles can be withdrawn,
   wherein when one or more of said articles are withdrawn from said container, each said withdrawn article is saturated with said solution.

2. The product of claim 1, wherein said substrate is one of a wipe, a towelette, a pad, a sachet, and a bandage.

3. The product of claim 1, wherein said concentration of the organo-functional silane-base quaternary ammonium salt is between about 1.0 percent and 1.7 percent inclusive.

4. The product of claim 3, wherein said concentration of the organo-functional silane-base quaternary ammonium salt is between about 1.3 percent and 1.4 percent inclusive.

5. The product of claim 3, wherein said solution is such that when said solution is applied to the surface and dries, an antimicrobial layer remains on the surface.

6. The product of claim 1, wherein said organo-functional silane-base quaternary ammonium salt is from the group consisting of 3-(trihydroxysilyl) propyldimethyloctadecyl ammonium chloride, octadecyldimethyl trimethoxysilylpropyl ammonium chloride, and combinations thereof.

7. A method of cleansing a surface, comprising
   withdrawing at least one of the articles from the product of claim 1;
   wiping the article on a surface, wherein said wiping transfers at least a portion of the solution including said organo-functional quaternary ammonium salt from the substrate to the surface so that a layer of solution is present on at least a portion of the surface; and
   drying said solution on said surface, wherein a semi-permanent layer of said organo-functional silane-base quaternary ammonium salt is fixed to said surface, said layer providing continuous anti-microbial protection after said drying occurs.

8. The method of claim 7, wherein said drying is accomplished through evaporation of the water from the solution at room temperature.

9. A method of making a substrate adapted to lay an antimicrobial solution on a surface, comprising:

applying a solution consisting of an organo-functional silane-base quaternary ammonium salt in a solvent, the solvent is at least about 90% water and optionally one or more phenol ethoxylates, polyethylene glycols, and/or polypropylene glycols, wherein the concentration of the organo-functional silane-base quaternary ammonium salt is between about 0.10 percent to 2.0 percent, and the solution is formulated for transfer of said organo-functional quaternary ammonium salt in solution to the surface from said substrate, to a flexible substrate consisting of a material without polyolefins, so that said substrate is impregnated with said solution and at least part of said solution remains in liquid form contacting or within said substrate, and wherein said applying includes said solution in an amount sufficient to transfer at least a portion of said solution from said substrate to a surface when said substrate is brought into contact with said surface, and wherein said solution and said substrate are packaged in a container that is initially substantially water tight.

10. The method of claim 9, wherein said organo-functional silane-base quaternary ammonium salt is from the group consisting of 3-(trihydroxysilyl) propyldimethyloctadecyl ammonium chloride, octadecyldimethyl trimethoxysilylpropyl ammonium chloride, and combinations thereof.

11. The method of claim 10, wherein the substrate is disposable and from the group consisting of wipes, bandages, pads, sachets, and towelettes.

12. The product of claim 1, wherein the solvent is at least about 95% water.

13. The product of claim 1, wherein the solvent is at least about 97% water.

14. The product of claim 1, wherein the solution consists of a suspension of the organo-functional silane-base quaternary ammonium salt dissolved in the solvent, and the solvent consists of water.

15. The product of claim 1, wherein the substrate includes a natural material from the group consisting of wool, silk, jute, hemp, cotton, linen, sisal, ramie, and wood pulp.

16. The product of claim 1, wherein the portion of the solution transferred to the surface includes an amount of the organo-functional silane-base quaternary ammonium salt, and wherein the amount is such that, if applied to and dried on clean dry glass slides, would result in an average contact angle on the slides of between about 80.4 degrees and 84 degrees.

* * * * *